United States Patent
Salter et al.

(10) Patent No.: US 9,376,704 B2
(45) Date of Patent: Jun. 28, 2016

(54) TEST KIT AND METHOD FOR DETECTING BACTERIOPHAGE

(75) Inventors: Robert S. Salter, Reading, MA (US); Gregory W. Durbin, Northboro, MA (US)

(73) Assignee: Charm Sciences, Inc., Lawrence, MA (US)

( * ) Notice: Subject to any disclaimer, the term of this patent is extended or adjusted under 35 U.S.C. 154(b) by 324 days.

(21) Appl. No.: 12/537,323

(22) Filed: Aug. 7, 2009

(65) Prior Publication Data

US 2009/0298051 A1   Dec. 3, 2009

Related U.S. Application Data

(63) Continuation-in-part of application No. PCT/US2008/001833, filed on Feb. 12, 2008.

(60) Provisional application No. 60/900,900, filed on Feb. 12, 2007, provisional application No. 60/905,707, filed on Mar. 8, 2007, provisional application No. 60/958,406, filed on Jul. 5, 2007, provisional application No. 61/018,789, filed on Jan. 3, 2008, provisional application No. 61/120,212, filed on Dec. 5, 2008.

(51) Int. Cl.
*C12Q 1/10* (2006.01)
*C12Q 1/22* (2006.01)

(52) U.S. Cl.
CPC .. *C12Q 1/10* (2013.01); *C12Q 1/22* (2013.01); *G01N 2333/245* (2013.01); *G01N 2333/938* (2013.01)

(58) Field of Classification Search
None
See application file for complete search history.

(56) References Cited

U.S. PATENT DOCUMENTS

| | | | |
|---|---|---|---|
| 5,527,667 A | 6/1996 | Ijzerman | |
| 5,605,812 A * | 2/1997 | Zomer | 435/38 |
| 5,643,743 A | 7/1997 | Chang et al. | |
| 5,728,542 A | 3/1998 | Charm | |
| 5,834,655 A | 11/1998 | Lad | |
| 5,914,240 A | 6/1999 | Sanders | |
| 5,935,799 A | 8/1999 | Isbister | |
| 5,958,675 A | 9/1999 | Wicks | |
| 6,090,541 A | 7/2000 | Wicks et al. | |
| 2004/0115378 A1 | 6/2004 | Dunaway et al. | |
| 2006/0040393 A1 | 2/2006 | Jia et al. | |

FOREIGN PATENT DOCUMENTS

| | | |
|---|---|---|
| WO | 9848042 A2 | 10/1998 |
| WO | 0179528 A1 | 10/2001 |

OTHER PUBLICATIONS

Stanek et al., Journal of Virological Methods, 2001, 91:93-98.*
Husimi, Yuzuru; Selection and Evolution of Bacteriophages in Cellstat; Advances in Biophysics, 1989; vol. 25; pp. 1-43.
Husimi, Yszuru et al; Cellstat—a continuous culture system of a bacteriophage for the study of the mutation rate and the selection process of the DNA level; Review of Scientific Instruments; Apr. 1982; vol. 53, No. 4; pp. 517-522; American Institute of Physics.
Lindemann, Bjorn F. et al; Evolution of Bacteriophage in Continuous Culture: a Model System to Test Antiviral Gene Therapies for the Emergence of Phage Escape Mutants; Journal of Virology; Jun. 2002; vol. 76, No. 11; pp. 5784-5792; American Society for Microbiology.
Schwienhorst, Andreas et al; Growth Kinetics of a Bacteriophage in Continuous Culture; Biotechnology and Bioengineering; Apr. 20, 1996; vol. 50 No. 2; pp. 217-221; John Wiley & Sons, Inc.
Sobsey; F+ RNA Coliphages as Source Tracking Viral Indicators of Fecal Contamination; University of New Hampshire; Dec. 2006; New Hampshire; US.
World Health Organization; Assessing Microbial Safety of Drinking Water—Improving Approaches and Methods; Nov. 2003; IWA Publishing; London; UK.
Stanek; Development of a Rapid Coliphage Detection Assay; Virginia Tech; Blacksburg, Virginia; US, (1997).
Pillai; Viruses in Foods; 2006; Chapter 8: Bacteriophages as Fecal Indicator Organisms; pp. 205-222; Springer; New York; US.
Reynolds; On Tap—Coliphage: A Better Water Quality Indicator; Water Conditioning & Purification; Sep. 2006; vol. 48; No. 9.
Love & Sobsey; Simple and Rapid F+ Coliphage Culture, Latex Agglutination, and Typing Assay to Detect and Source Track Fecal Contamination; Applied and Environmental Microbiology; Jul. 2007; vol. 73; No. 13; pp. 4110-4118; American Society for Microbiology; Washington D.C.; US.
Young; Bacteriophage Lysis: Mechanism and Regulation; Microbiological Reviews; Sep. 1992; vol. 56; No. 3; pp. 430-481; American Society for Microbiology; Washington D.C.; US.

* cited by examiner

*Primary Examiner* — Nicole Kinsey White
(74) *Attorney, Agent, or Firm* — MacCord Mason PLLC; Richard J. Long

(57) ABSTRACT

Phages can be detected as rapid indicators of the hygienic quality of a sample. Both continuous flow methods and devices, single sample methods and devices, of various volumes, can be used. Single samples may be tested by single or multi-step testing methods. Test kits can be provided in easy-to-use formats. Certain phages, such as coliphage, are useful as indicators of fecal contamination.

19 Claims, 9 Drawing Sheets

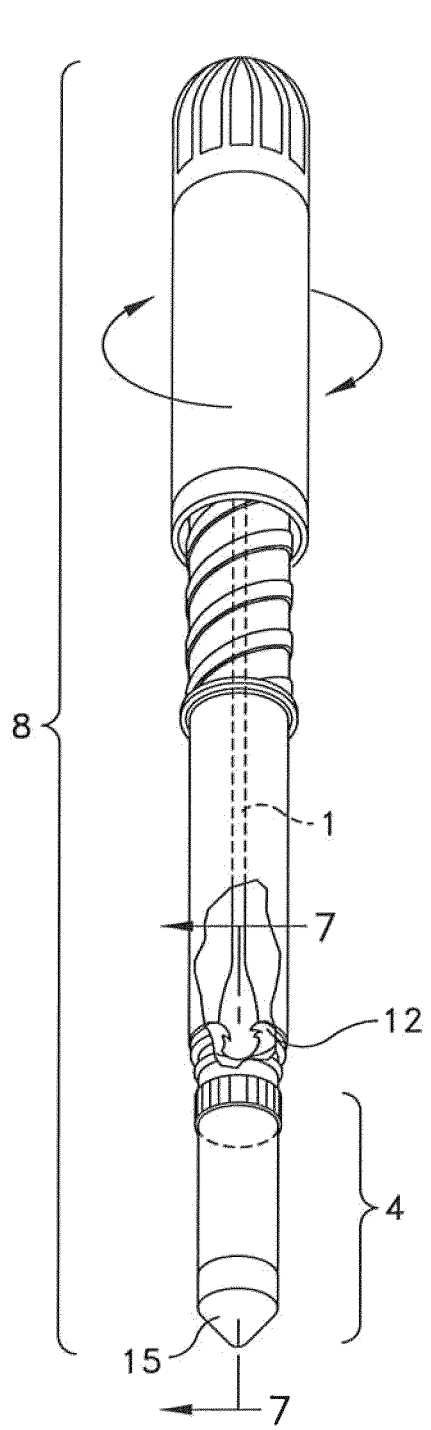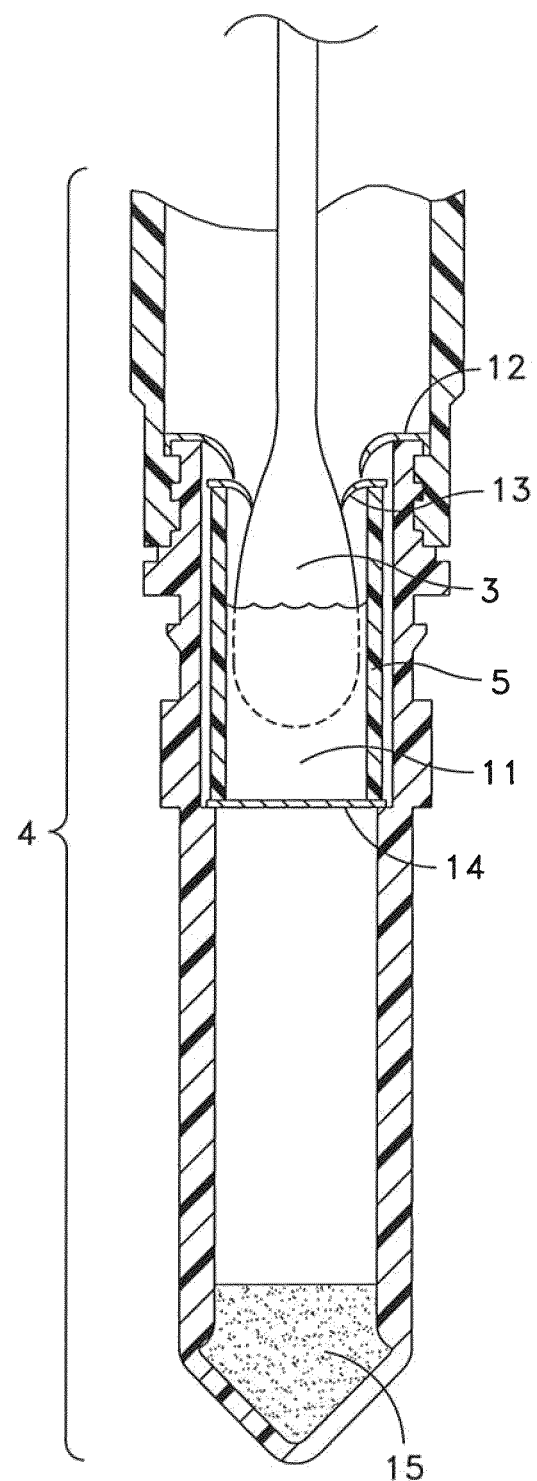
FIG. 8
FIG. 9

TEST KIT AND METHOD FOR DETECTING BACTERIOPHAGE

REFERENCE TO PRIOR APPLICATIONS

This application is based on and claims priority to and is a continuation-in-part of, PCT/US08/01833, filed Feb. 12, 2008, which further claims priority to U.S. Provisional Application No. 60/900,900, filed on Feb. 12, 2007; U.S. Provisional Patent Application No. 60/905,707, filed on Mar. 8, 2007; U.S. Provisional Patent Application No. 60/958,406 filed Jul. 5, 2007; and U.S. Provisional Patent Application No. 61/018,789 filed Jan. 3, 2008, all of which are hereby incorporated by reference. This application also claims priority to U.S. Provisional Patent Application No. 61/120,212, filed Dec. 5, 2008, which is hereby incorporated by reference.

BACKGROUND

Bacteriophage (phage) are viruses that infect bacteria. Phage can be grouped by the types of bacteria they infect. For example, certain types of phages, referred to as coliphage, infect coliform bacteria. The lytic cycle of coliphage replication cause the cell to lyse and release its contents, including intracellular enzymes.

In environmental water and some food samples the presence of $E.$ $coli$ is an indicator of fecal matter. The Environmental Protection Agency interprets the presence of coliphage in groundwater as an indicator of the presence of fecal matter that is equivalent to detection of $E.$ $coli$ and Enterococci. The equivalence of coliphage as an indicator reflects the idea that the presence of viruses to coliform bacteria must indicate the current or prior presence of coliform bacteria. In foods such as produce, coliphage detection may be useful as an indicator of hygienic production and cleanliness.

Like bacteria, such as pathogenic bacteria, found in fecal matter, viruses, such as enteric viruses, found in fecal matter can pose health risks for humans. Coliphage are an extensive and diverse group of viruses that include medium and large DNA viruses, small genome DNA viruses, and double and single stranded DNA and RNA viruses. Many coliphage are of roughly the same size, molecular weight and nucleic acid contents as enteric viruses and they occur in larger numbers. Coliphage, therefore, can be used as surrogate indicators for the possible presence of human pathogenic viruses.

We describe herein easy-to-use systems, methods and apparatuses for rapidly qualitatively and quantitatively detecting phage, particularly coliphage.

BRIEF DESCRIPTION OF THE DRAWING

FIG. 8 shows the swab tip 3 puncturing the top seal 13 of the optional niblet.

FIG. 9 is a cross-section showing the swab tip 3 puncturing the top seal 13 of the optional niblet.

SUMMARY

Figures 1, 2:
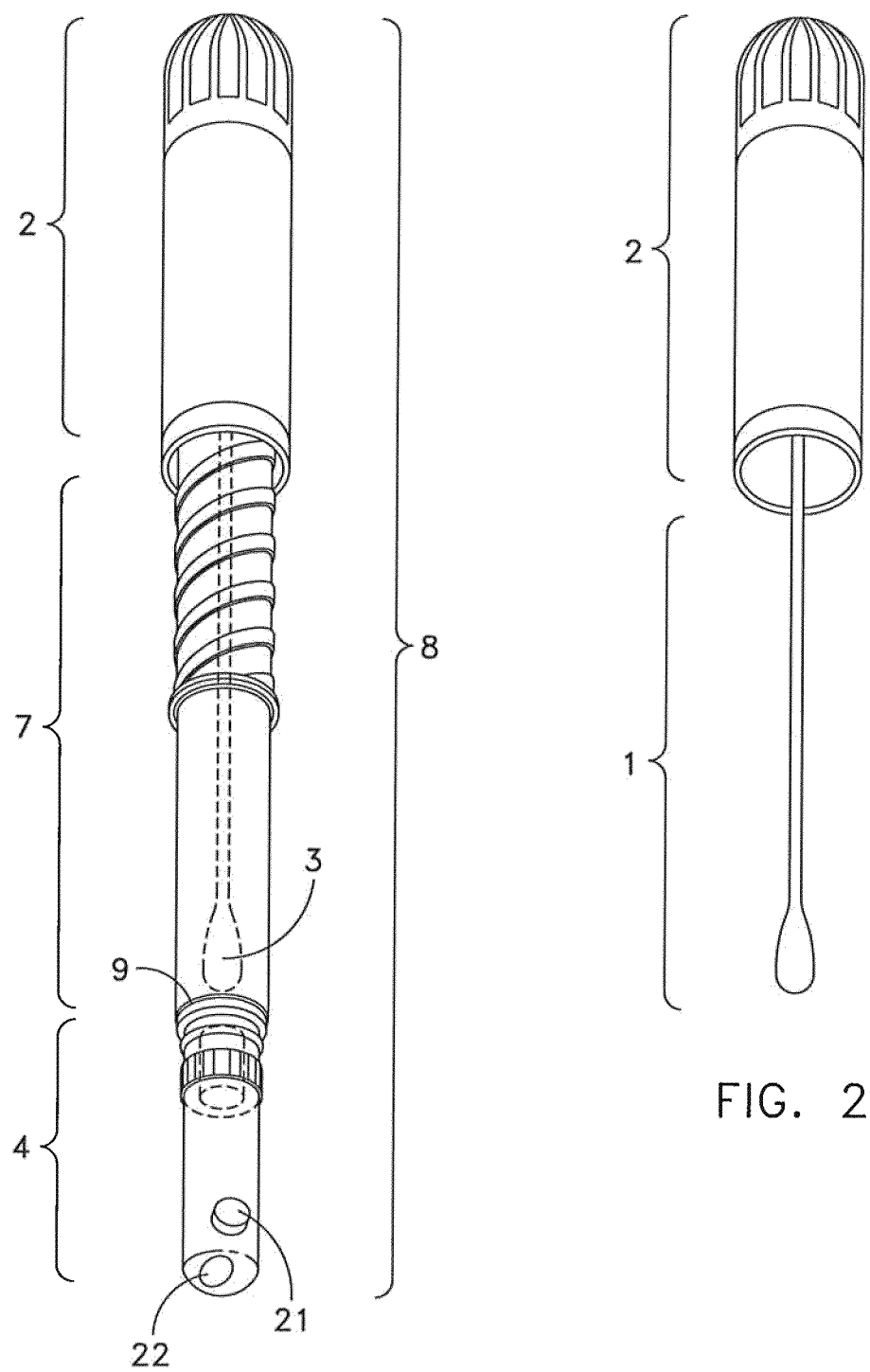
FIG. 1 shows the PocketSwab style format test unit 8 with media tablet 21 and $E.$ $coli$ tablet 22 in the bottom vial 4.
FIG. 2 shows the swab 1 and swab tip 3 removed from the test unit 8.

An aspect includes growing an $E.$ $coli$ culture to an appropriate concentration. The culture is then freeze dried. Freeze drying conditions can be chosen to enhance cell stability. The freeze dried culture can be supplied to the end-user in combination with appropriate freeze dried media. The media can contain one or more growth indicators, such as calorimetric and/or fluorogenic enzyme substrates. The culture can be supplied to the end-user either mixed with the media or in separate containers or in separate tablets. If multiple media addition steps are used, whether or not each step utilizes the same media, the media for each step can be supplied separately.

When water samples are to be tested for fecal contamination the sample can be used to rehydrate the $E.$ $coli$ culture and media. The culture and media can be packaged separately or together in dissolvable bags that, upon contact with a liquid such as a liquid sample, or upon contact with a liquid and after heating (incubation), the packaging dissolves allowing the sample to contact the culture and the media. The dissolvable bags can be provided to the user within a variety of possible containers. Saline may also be used to rehydrate culture before addition to a water-sample-media-mix. During incubation, if coliphage is present in the water sample, they will infect the $E.$ $coli$ and form multiple copies. Typically, cell lysis of the $E.$ $coli$ cells follows infection. Lysis of the $E.$ $coli$ cells releases intracellular enzymes such as β-galactosidase. Media components can be optimized for detection of phage using a single media addition step. Alternatively, multiple media addition steps can be employed. In some aspects the multiple media addition steps can contain similar media. In other aspects, the first media addition step can include media components configured for optimum $E.$ $coli$ replication and the second media addition step can include media components configured for optimum $E.$ $coli$ cell lysis and phage detection. When an appropriate indicator reagent, such as calorimetric and/or fluorogenic enzyme substrates, are included in the media, a detectable change occurs, for example via the enzymatic action of β-galactosidase on the indicator reagent. Such indicators can be used alone or in combination to provide multiple test interpretation options, for example combining calorimetric and fluorogenic indicators. If coliphage are not present then indicator release into solution is relatively slow and no change will be observed during the testing period; the sample will appear turbid as the bacteria multiply and detectable changes (due to indicator reactions) are much slower as compared to if the bacteria were lysed by phage. When bacteria are lysed detection times are in the range of about 2 hours to about 8 hours, for example 4 hours. When media is added in multiple steps *E. coli* growth can be optimized in a first step and a second media addition step can be used to reduce background fluorescence from *E. coli* and, therefore, extend test time. Alternatively, the second media step can include indicators not present in the first media step. In either case, multiple step media addition can be used, in particular, to detect less prolific phage.

The method and apparatus can be provided to customers in an easy-to-use kit form for a variety of applications. Such kits can include bottles for testing, media, culture, saline and control. The media and culture can be in dried and in tablet, powder, concentrated or gelatinous form. Dissolvable bags can be used with either powders or tablets to prevent human contact.

One application is as an indicator for fecal contamination in groundwater. Other suitable matrices for testing include produce (fruits and vegetable), recreational (swimming) water, farm ruminant, water effluents, waste water and shell fish. Generally, the method and apparatuses can provide users with a rapid, easy-to-use method of measuring the hygienic quality of a sample.

Embodiments include qualitative and quantitative (most probable number-MPN or plaque forming units-pfu) results. For qualitative testing, a solution in a single container can be used and changes observed in that container. Multiple step media may be employed, for example, with a first media used for optimization of *E. coli* growth and phage replication and a second media used for phage induced *E. coli* lysis and released enzyme detection. Alternatively, a sample may be tested in multiple steps by combining the bacteria culture with the nutrient media and then combing a portion of that mixture with a second media and the sample. The test may be conducted in one container or, if using multiple steps, multiple containers. Container sizes can be varied including, for example, standard sample sizes such as 0.5 ml, 1 mL and 100 mL sample sizes. Smaller sample sizes can be accommodated in single service devices such as the POCKETSWAB (POCKETSWAB is a registered trademark of Charm Sciences, Inc. Lawrence, Mass.) style test device. Particularly for larger sample sizes, such as 100 mL, dissolvable containers, such as dissolvable bags or pouches, may be useful. Such dissolvable containers include those made from polyvinyl alcohol film. Such containers can be water soluble and can be used to package either media or culture separately or as a mixture. The bags can be dissolvable upon contact with water or, alternatively, be dissolvable upon contact with water above a certain temperature. For testing the dissolvable bags can be placed in an appropriate container, or delivered to the end-user in an appropriate container. When the sample is added to the container, or after heating, the bag will dissolve. Dissolution of the bag will allow the media and/or culture to contact the sample. Possible packaging material includes ELVANOL (ELVANOL is a registered trademark of E. I. DU PONT DE NEMOURS AND COMPANY CORPORATION DELAWARE). The dissolvable bag can be used to limit or prevent human contact with test materials including the media and culture. Such contact being through skin or inhalation of powder plume when poured.

For quantitative results, a variety of MPN formats are useful including traditional test tube division and compartmenting devices, such as the QUANTI-TRAY (QUANTI-TRAY is a registered trademark of Idexx Laboratories, Westbrook, Me.), SIMPLATE (SIMPLATE is a registered trademark of Idexx Laboratories, Westbrook, Me.) and TEMPO (TEMPO is a registered trademark of bioMerieux CORPORATION Chemin de l'Orme Marcy-L'Etoile FRANCE) devices. Another format includes adding a gelling agent, such as alginate, such as that described in U.S. Pat. No. 5,605,812, incorporated herein by reference. The gellable material can be included with the media and culture in a plastic bag along with a solid grid-like device, matrix, such as a plastic grid. Mixing of the sample in the bag with the media and culture will separate the mixture into compartments within the solid grid. Detectable changes will then be observable in separate grids providing the ability to quantitate.

Another aspect includes a continuous flow system that can be used to monitor a water supply or test multiple samples. Such methods and devices can provide customers, for example water authorities, a rapid, easy-to-use method of continuously monitoring the hygienic quality of a sample, a series of samples or a continuous flow of material to be tested. The method can include combining, within a first container, a sample with a media to form a first admixture, the first container having an outlet, the media comprising nutrients for the growth of *E. coli*, induction agents and an indicator for the presence of an *E. coli* enzyme, such as β-galactosidase. The first admixture flows, for example via a pump, into a second container to form a second admixture. The second container can be continuously mixing or stirring. The second container includes an *E. coli* culture undergoing exponential growth, a second container inlet and a second container outlet. The second admixture can be removed from the second container at approximately the same rate at which the first admixture flows in. In addition, the *E. coli* culture can be removed at a rate approximately equivalent to the rate at which said *E. coli* is dividing to maintain a stable concentration range and stable growth phase, such as log phase. The second admixture is incubated within the second container to facilitate the growth of the culture. The optical density of the second admixture can be monitored to provide feedback and thereby control, such as through a signal to a pump, the flow rate of the first admixture into the second container and the removal rate of the second admixture from the second container. If coliphage is present in the first container then when the coliphage enters the second container the *E. coli* therein will be infected and will be lysed. Intracellular enzyme that is released by the lysis can be measured by the affect of such enzyme on the indicator. The presence of coliphage in the sample is used as an indicator of fecal contamination within the sample. Additionally, the growth rate of the phage is faster than the replication rate of the *E. coli* and, therefore, the *E. coli* will lyse faster than they replicate. The resulting rapid decrease in absorbance and a shutdown of the flow through system can be used as an indicator just as fluorescence and/or color changes are used as indicators.

Measurements such as optical density, fluorometric, calorimetric measurements can be taken directly from the second admixture or can be taken after the second admixture flows out of the second container. Flow out of the second container can be to waste and can include a diversion to measuring instrumentation such as fluorometers, spectrophotometers and the like. Examples of appropriate flow control mechanisms include various pumps and valves such as a throttling valve. Such flow control mechanisms can be, in a closed system, before or after any of the containers described. Such flow control devices can also be located upstream within the source of sample for the system described herein, such as a throttling valve within an upstream higher pressure water delivery pipe.

By adding a sample to a device that includes a culture already in log phase, rapid detection of coliphage can occur, for example in less than 8 hours. In some aspects detection can be in 25 minutes or less.

Certain aspects include flowing sample continuously, through a first container inlet, into a first container and flowing media continuously, through a second container inlet, into a first container. In such a method a continuous flow of sample could be monitored.

Certain aspects include maintaining bacteria at an optimum stage for phage infection to add robustness to the system. Addition aspects include maintaining bacterial growth at a phase to prevent acidification of the system and loss of fluorescence signal. High cell concentration can also result in an increase in background fluorescence from, for example, leaking of enzyme from $E.\ coli$. Such background fluorescence or acidification can inhibit detection. By providing a system with multi-step media addition, fewer and/or less prolific and/or less lytic phage, may be detected by extending testing times beyond 6 hours, for example to 8 hours. Such time from infection extension might not be possible with a static system in which background fluorescence, from the media formulation, growth and natural (non-phage induced) lysis or leaking of $E.\ coli$ cells, limits detection.

DETAILED DESCRIPTION

Some embodiments utilize somatic or male specific coliphage-induced lysis and release of β-galactosidase from $E.\ coli$ strain C(CN-13) or $E.\ coli$ strain $F_{AMP}$ or other host $E.\ coli$ strains. A benefit of using these strains is their antibiotic resistance. Contaminated samples containing coliform may have phage resistant forms that could grow and compete with the host bacteria presented. The antibiotics impart competitive growth advantage to the host against contaminated samples. It should be understood, however, that multiple strains of $E.\ coli$ or enteric bacteria, for example $E.\ coli$ strain C (ATCC 13706), $E.\ coli$ strain C (ATC 700609—nalidixic acid mutant of ATCC 13706) and other mutants thereof that are infected by bacteriophage, and which produce indicators, can be employed.

In an embodiment $E.\ coli$ are cultured to a target concentration, stabilized (to prevent leakage of intracellular content) and then freeze dried for storage until ready for use. Culturing can occur in flasks or fermentors. For $E.\ coli$ strain C (ATCC 13706) the standard nutrient broth recommended by ATCC can be used with 0.5% NaCl. It may also be possible to increase the level of β-galactosidase in the cells by culturing in an environment that promotes β-galactosidase production, for example by culturing in certain carbohydrate-deprived media with the presence of an inducer compound.

After freeze drying, either or both the bacteria and media can be concentrated to provide an easy-to-use premeasured amount to the end-user. A combination of tablets, gels and freeze dried powder can also be used. For example, tableted $E.\ coli$ culture and freeze dried, untableted media. Freeze dried media and $E.\ coli$ can also be simply combined without tableting. Dried media and dried $E.\ coli$ can also be provided in separate sealed bags. For example, water soluble bags that dissolve upon contact with sample or upon contact with sample and the addition of heat.

In an embodiment, the starting concentration of $E.\ coli$ in the test is about $10^4$ cfu/ml to about $10^8$ cfu/ml. The sample size must also be considered so that, for example, if the starting test concentration of $E.\ coli$ is $10^6$ cfu/ml, and the test will be rehydrated with 100 ml, the concentration of freeze dried $E.\ coli$ provided can be $10^8$ cfu per volume of dried material (such as tablet) so that the final test concentration is $10^6$ cfu/ml. Similarly, when rehydrated with 1 ml, the freeze dried concentration can be $10^8$ cfu per volume dried material. The concentration of $E.\ coli$ may be reflected in test result time. For example, more concentrated $E.\ coli$ may provide faster test results. Higher concentrations, however, may make the test less sensitive to low viral content.

A water sample can be added to the combination of media and a dried $E.\ coli$ cell culture that includes a concentration of cells, in the range of about $10^4$ to about $10^8$ cells. If coliphage are present in the water sample they will infect the $E.\ coli$, multiply within the $E.\ coli$ host, and lyse the $E.\ coli$ cells causing the release of the intracellular material, including enzymes such as β-galactosidase, into the surrounding medium. β-galactosidase in the surrounding medium will react with appropriate enzyme substrate, such as colorimetric, fluorogenic, or both, whereas intracellular β-galactosidase does not pass through an intact cell wall or cell membrane. Thus, no reaction will occur unless the β-galactosidase is outside the cell. In addition, generally in conjunction with the color or fluorogenic color development, high concentrations of coliphage, for example greater than $10^6$ cfu/ml, will result in immediate $E.\ coli$ lysis and the lack of $E.\ coli$ growth. The lack of $E.\ coli$ growth will produce a sample that has a clear appearance as compared to the turbidity of the sample in which $E.\ coli$ is growing in the absence of coliphage. However, in the presence of a high concentration of coliphage, such as in highly polluted samples, the sample may not detectably change and will just become clear. In such a case, the $E.\ coli$ are lysed quickly before having time to express sufficient β-galactosidase to generate a visible change. Even in such circumstance, the clarity of the sample, as compared to a turbid negative control, will be easily interpreted as a positive result.

A variety of media, that will support the growth of $E.\ coli$, are usefully employed in the media/sample reservoir. Generally, relatively rich media containing carbohydrates, amino acids, and vitamins are useful. For either $E.\ coli$ strain C or CN-13 the standard nutrient broth recommended by ATCC can be used with 0.5% NaCl. A goal in selecting media is to enhance target enzyme production, such as β-galactosidase production, and to limit the available carbohydrate, other than the color or fluorescent indicator(s), upon which β-galactosidase can act. To enhance β-galactosidase the media can include synthetic inducers. Two known synthetic inducers of β-galactosidase are isopropyl-β-D-thiogalactoside (IPTG) and methyl-β-D-thiogalactoside (TMG). Other useful media components include: magnesium sulfate and calcium chloride, which may aid the coliphage binding to and infecting $E.\ coli$; a relatively rich broth such as brain heart infusion and yeast extract which may provide nutrients to help maintain the cell wall and, thereby, prevent the premature leakage of β-galactosidase in negative samples and negative controls. It is possible to separate the various media components into sequential steps to optimize phage detection. For example, a first step can include rich media with carbohydrate and β-galactosidase inducers and a second step can be less media rich but include one or more β-galactosidase detection substrates. One or more color or fluorogenic indicators may be included as part of the media. Alternatively, each of the media steps can include similar media and serial transfers simply serve to reduce test background and, thereby, enhance detection.

Examples of calorimetric reagents which can be employed as substrates for β-galactosidase include O-nitrophenyl-β-D-thiogalactoside (ONPG), 5-bromo-4-chloro-3-indoyl-β-D-galactoside (X-GAL), and chlorophenol red β, D-galactopyranoside (CPRG). Other possible indicators include glucuronidase, α-galactosidase, chlorophenol red B-D-galactopyranoside, glucosidase, escalinase, pH and optical density. If the β-galactosidase is released into the medium, it will cleave the calorimetric reagent and a detectable colored reaction will occur. If no coliphage is present in the water sample, β-galactosidase will not be released into the medium and any color change will be much substantially slower and the sample turbidity will be constant. That is, during the specified time for coliphage detection, substantial color development will not occur in a sample that does not contain coliphage.

It is recognized that there are other enzymes, and there may be new or well known fluorogenic and chromogenic substrates for β-galactosidase and other enzymes, which could provide identification of E. coli with different color or change in color. Thus, the media identification substrate to be used can vary. An example of a useful fluorogenic substrate is 4-Methylumbelliferyl-β-D-galactopyranoside (MUG-GAL). It may also be possible to use other indicators of E. coli growth, or lack thereof, including calorimetric, fluoregenic, pH indicators and oxidation/reduction indicators. Indicators, such as a color change, fluorescence, pH or optical density, can be used to indicate E. coli lysis or change in the E. coli growth pattern.

It may also be possible to combine indicators, such as combining color indicators with fluorogenic indicators. By combining indicators, for example with an indicator that is visible to the eye under ambient light, and an indicator that requires some instrumentation but may be more sensitive, the user can be provided more flexibility. This is particularly feasible when inducing enzyme production, such as galactosidase with IPTG, and using MUG-GAL as a fluorescent indicator of cell lysis. It may be further beneficial to combine the calorimetric indicator X-GAL with the fluorogenic indicator MUG-GAL.

The dried material (bacteria and media) can be supplied to the end-user in a variety of configurations. For larger sample sizes, such as may be appropriate for testing drinking water, a sealed plastic bag or screw top container can be used. Screw top containers can include a vented cap to provide an opening for gas exchange. For smaller sample sizes, a vial-type container can be used, for example, in a POCKETSWAB type device format described in U.S. Pat. No. 5,965,453 incorporated herein by reference. When multiple media addition steps are employed, the multiple medias, whether the same or different, can be supplied separately.

One useful container is a transparent, flexible, throwaway, plastic, sealable bag which contains the dried test composition such as the ECOLITE (ECOLITE is a registered trademark of Charm Sciences, Inc. Lawrence, Mass.) described in U.S. Pat. No. 5,728,542 incorporated herein by reference. To use, the bag is unsealed, and a defined amount, such as for example, 100 ml of the water sample is poured into the bag. The bag is then closed tightly by folding tightly, for example with a wire strip or other sealing means, to form a water tight seal. With the bag closed, the user thoroughly mixes the reagent medium. The bag with the dry medium, dried microbial culture and the water test sample is sealed and incubated at about 37° C.±2° C., for about 2 to about 8 hours depending on instructions provided with the test. Color or other indicator change during that time period indicates the presence of coliphage and, therefore, the presence of fecal contamination. If no change occurs during the testing time, and the sample appears turbid, coliphage is not present in the sample. In a highly contaminated sample in which high concentrations of coliphage quickly lyse the E. coli cells in the culture, the sample may appear clear with no changes, for example no color development.

Rather than have the media and/or culture supplied directly in the container within which testing will be conducted, the media and/or culture can be provided in a separate sealed container such as a tearable container. The media and/or culture can also be supplied in dissolvable bags within, for example, the tearable container. In such an embodiment, the tearable or pealable container or blister pack would be torn and the media added or the dissolvable bag(s) added to a separate sealable plastic bag, or screw top solid container, such as a screw top container that can hold approximately 100 mL to 200 mL of liquid, within which has been added the liquid sample to be tested. The dissolvable bag is particularly useful for use with the culture to prevent or limit human contact with the culture. In addition, tablets can be used, with or without dissolvable containers. The tablets can contain freeze dried E. coli culture and/or media. The tablets can be added first to saline or, if culture, to media and rehydrated and/or incubated before adding as a liquid.

Larger sample sizes for which quantitation is desired, such as 100 mL samples, after rehydration, can be aliquoted into multiple containers for MPN analysis. For example the sample can be poured into a device such as that known as the QUANTI-TRAY and described in Naqui et al., U.S. Pat. No. 5,518,892, incorporated herein by reference. The apparatus features a plastic form which is designed for receiving a liquid sample and subsequently distributes the liquid sample into separate compartments within the plastic form so that different aliquots of one or more sizes may be tested. The quantifying step involves detecting the quantity and quality of the color, or other change in each compartment, and comparing that quantity and quality to an MPN table.

Using the QUANTI-TRAY format with the herein described phage detection method and device. The presence of turbidity and absence of color, fluorescence, or other indicator, in the developing well of the Naqui device indicates that coliphage is not present in the sample: that coliphage are not present thereby allowing the E. coli culture to grow unimpaired by coliphage. Each compartment of the Naqui invention that clarifies or otherwise changes can be observed and the result in each counted to arrive at a coliphage MPN result. Other smaller volume MPN type devices that may be useful include the SIMPLATE devices and TEMPO (TEMPO is a registered trademark of bioMerieux CORPORATION Chemin de l'Orme Marcy-L'Etoile FRANCE). Users may also simply aliquot by pipetting into multiple test containers prior to test incubation.

Using the POCKETSWAB format the dried material can be provided in two separate tablets: a media tablet and a bacteria tablet. A variety of possibilities for obtaining a sample include removing the vial portion of the POCKETSWAB device and using it to "scoop" a liquid sample into the vial. The vial portion can then be replaced and the swab, or probe, provided with the device used to puncture the membrane seals to contact the sample with the dried or tableted media and culture. Similarly, a sample can be pipetted into the vial. Alternatively, the swab portion of the device containing a liquid, such as a buffer, portion above the tablets can be used to absorb a sample, for example, from a vegetable rinse, spinach leaf or mollusk stomach. The swab can be used to puncture the various compartments within the vial thereby allowing the buffer-sample mixture to contact the media and culture. When the swab is used to absorb a sample, additional liquid may be required, either from another sealed compartment within the device, for rehydrating the media and culture.

The format of the POCKETSWAB provides the advantage of controlled movement of the probe in a test device that provides physical support for the probe and compartments for storage of reagents and sample addition.

Depending on the disposal and other potential contamination issues involving culturing *E. coli*, it may be useful to employ a device, such as described in International Patent Publication WO/2006/069053, published Jun. 26, 2006, hereby incorporated by reference. It may also be useful to include a bactericide and/or viricide to provide the end-user with a convenient method for killing the culture and/or phage after test operation.

In another example of use for pfu/ml quantitation, a gelling agent may be useful, such as available in the COLIGEL (COLIGEL is a registered trademark of Charm Sciences, Inc., Lawrence, Mass.) format described in U.S. Pat. No. 5,605,812 incorporated herein by reference. In such an embodiment, coliphage presence will be indicated by detectable change in the gel media. Quantitation may also be possible in such a format by counting the spots, such as spots of color, in the gel.

The methods and devices described herein are largely directed to detecting somatic coliphage in an *E. coli* culture through the action of the *E. coli* enzyme β-galactosidase. Those skilled in the art will appreciate that detecting other phages, such as male F+ coliphage, can similarly be used to indicate the presence of the phage susceptible bacteria or the sample environment to which the presence of such bacteria can be related. Similarly, other enzymes and indicators may be usefully detected as indicators of cell lysis.

By utilizing the various methods and devices described herein, detection of a contaminated sample can occur rapidly, for example in less than 8 hours, preferably in less than one hour. By utilizing multiple media addition steps, low level contamination and/or contamination with less lytic and/or less prolific phage, can be more sensitively detected. For example in some conditions a single phage can infect a cell and replicate 100 or more progeny in as little as 10 minutes. After 20 minutes 10,000 progeny could be produced and in 30 minutes 1,000,000 progeny could be produced. Thus, detection can occur in less than about 30 minutes from initial infection. Such rapid detection is achieved by flowing sample continuously into a culture that has been established in log phase growth and detecting the lysis of the cells in the culture by infecting phage. The culture can be grown separately and then added to a container that is maintained at an appropriate temperature for *E. coli* growth, for example about 37 degrees C. (the culture container). In an embodiment the target concentration of *E. coli* in the test is about $3 \times 10^7$ cfu/mL to $8 \times 10^7$ cfu/mL. The culture container can be flowably connected to a media/sample reservoir. A pump can be used to pump the contents of the media/sample reservoir into the culture container.

The media/sample reservoir can be fed by a media container that can include a selected, appropriate media. The media/sample reservoir can also be fed by a sample container that can include a sample to be tested. The sample container can also include, instead of the sample, a negative or positive control. An example of a negative control is sterile water. The media/sample reservoir can be flowably connected to the culture container through an outlet from the media/sample reservoir. In an embodiment of a continuous flow system, in which a stream of sample is provided, the media/sample reservoir can also be connected to a sample source for example through inlets into the media/sample reservoir. Such an inlet can be used to provide sample continuously or, for example, until a positive result is found at which time flow of sample can be stopped either automatically or manually.

After the culture within the culture container is stabilized at approximately the target cell concentration, sample mixed with media can be added. During incubation, if coliphage is present in the water sample, they will infect the *E. coli*, form multiple copies, and subsequently lyse the *E. coli* cells. Lysis of the *E. coli* cells releases intracellular enzymes, such as induced enzymes, including β-galactosidase. When an appropriate indicator reagent, such as calorimetric and/or fluorogenic indicators, are included in the media, a detectable change occurs, for example via the enzymatic action of β-galactosidase on the indicator reagent. In an alternative embodiment, to prolong the point at which test background overwhelms the system, a portion of the growing culture may be added to fresh uninoculated media.

It may be further beneficial to combine a calorimetric indicator such as X-GAL with a fluorogenic indicator such as MUG-GAL. For example, it may be possible to enhance fluorescent results, particularly the fluorescent color in negative results, through the use of a calorimetric indicator, such as X-GAL, with a fluorescent indicator, such as MUG-GAL. If coliphage are not present, then the indicator release into solution is relatively slow and no change will be detected. If coliphage are present, then bacteria are lysed and the enzyme is released into the outer media where it can act on the indicator.

As media/sample flows from the media/sample reservoir into the culture container, outflow from the culture container removes sufficient amount of culture to maintain the culture within the culture container at a relatively steady stage of growth and concentration. That is, as the *E. coli* are dividing, the rate of flow of media and sample into the culture container, and the rate of flow of culture out of the culture container, are adjusted to maintain the concentration at a relatively steady concentration and in log phase of growth. The culture container can be sealed to prevent contamination, in which case the in flow rate is approximately equal or exactly equal to the outflow rate. Monitoring of the growth of the cells can be by methods known to those skilled in the art, such as optical density.

The outflow can be to a waste container. The outflow can also flow into an intermediate container between the culture container and the waste container. The intermediate container can be positioned relative to a spectrophotometer so that the spectrophotometer can be used to determine the optical density (OD) of the material which is used as an indicator of the culture concentration. The appropriate OD can be maintained, for example OD520, by a feedback loop that controls a pump or other flow control device such as a control valve, for example a peristaltic pump, positioned between the media/sample reservoir and the culture container or anywhere in the closed system. Similarly, the signal from the material, such as fluorescence and/or calorimetric, can be determined at the intermediate container by an instrument such as a fluorometer, calorimeter or spectrophotometer. By having the media/sample reservoir, culture container and waste container flowably connected, a continuous flow of samples for detection can be achieved. For example, a water authority could continuously sample its water supply by diverting water samples into the system for continuous detection.

After a positive sample is detected a continuous flow system must be cleaned. Some embodiments include a clean in place system to allow the entire flow path to be cleaned before new sample is introduced. Other embodiments include a disposable flow path that can be replaced periodically and/or when a positive sample flows through and thereby contaminates the system.

The methods and devices described herein are largely directed to detecting somatic coliphage in an *E. coli* culture through the action of the *E. coli* enzyme β-galactosidase. Those skilled in the art will appreciate that detecting other phages, such as male F+ coliphage, by changing host bacteria and selective media components, can similarly be used to indicate the presence of the phage susceptible bacteria or the sample environment to which the presence of such bacteria can be related. Similarly, other enzymes and indicators may be usefully detected as indicators of cell lysis. In addition, there will be a measurable OD decrease as the cells lyse and in an automated system this will reduce the inflow rate.

DETAILED DESCRIPTION OF THE DRAWINGS

FIGS. 1-10 show the method in a PocketSwab style test device. Such a device can be used for small sample sizes of about 0.5 mL to about 1 mL. For larger sample sizes, for example 100 mL, a screw top container 53 or plastic bag device 56 can be used.

FIG. 1 shows the PocketSwab style format test unit 8 with media tablet 21 and *E. coli* tablet 22 in the bottom vial 4. FIG. 2 shows the swab 1 and swab tip 3 removed from the test unit 8. The swab tip 3 can be used to absorb a sample, for example from a spinach leaf or other material to be tested. In some embodiments the swab tip 3 is unnecessary, such as when the vial 4 is used to "scoop" a sample or if the sample is pipetted into the vial 4, in such embodiments the swab 1 can be simply a probe to puncture the seals in the vial and need not include an absorbent tip.

Figure 3:
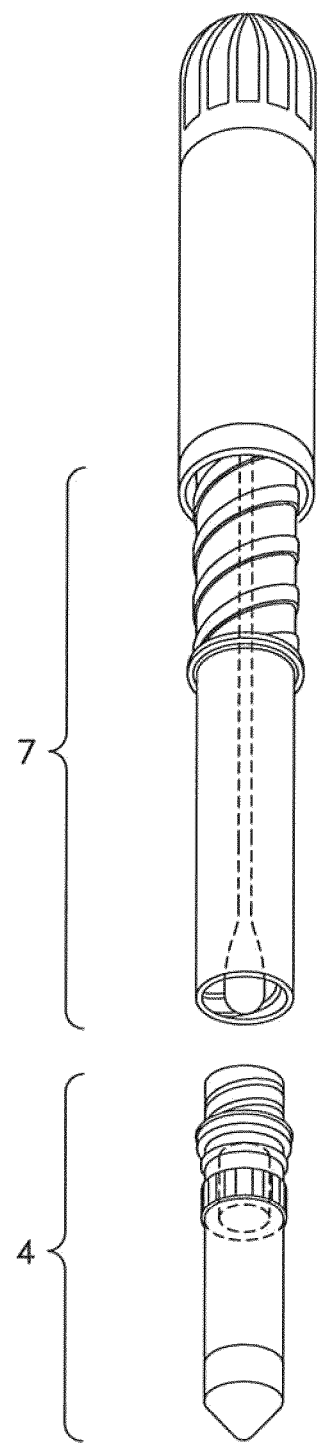
FIG. 3 shows the bottom vial 4 separated from the swab body 7.

FIG. 3 shows the bottom vial 4 portion separated from the swab body 7. The vial portion can be threadably attached to the swab body 7 for easy removal and use either to "scoop" a sample or to allow access to the media/culture in the vial 4 other than by using the probe 1. In embodiments in which a sample is pipetted into the vial 4, no probe is required and the seal can be punctured with, for example, a pipette tip.

Figure 4:
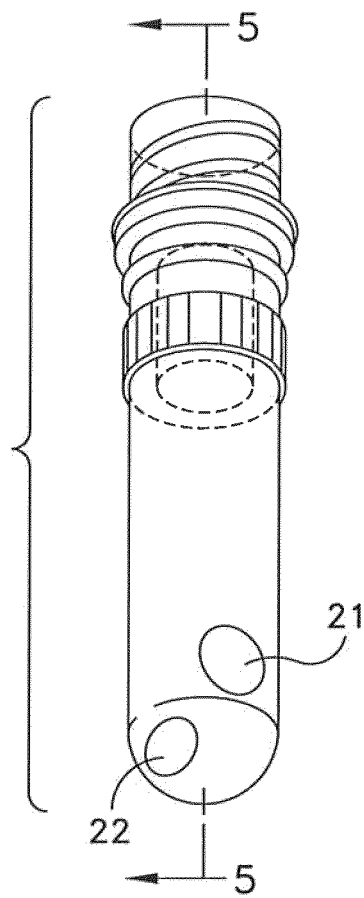
FIG. 4 shows the bottom vial 4 with media tablet 21 and $E.$ $coli$ tablet 22.
Figure 5:
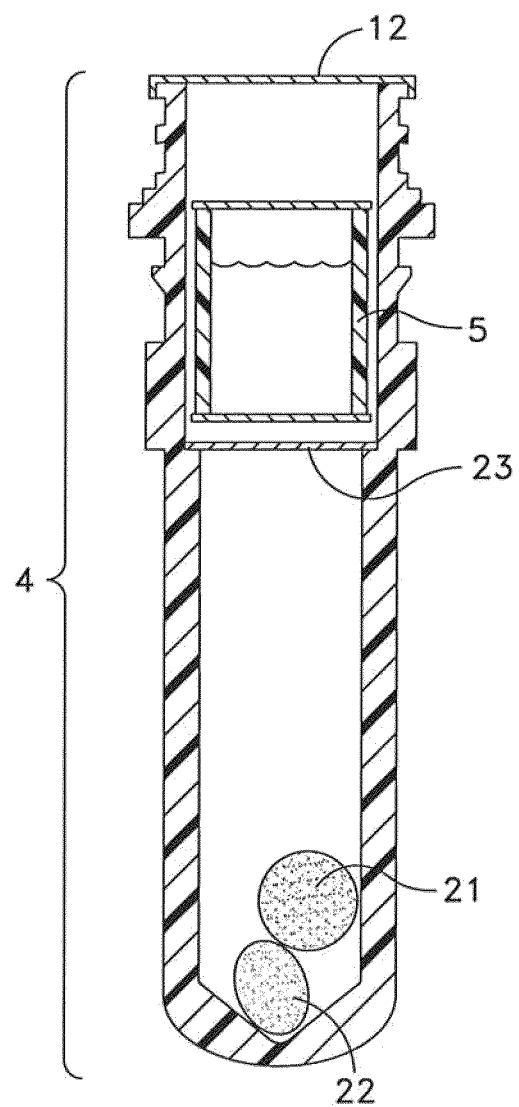
FIG. 5 is a cross section of the bottom vial 4. Also shown is an optional niblet 5 containing liquid for rehydrating tablets 21 and 22.

FIGS. 4 and 5 show the bottom vial 4 portion with media tablet 21 and *E. coli* tablet 22. The optional niblet 5 is also shown. If additional liquid, such as buffer, is not required to rehydrate the media/culture tablets 21, 22 or powdered media/culture mixture 15, the niblet 5 can be excluded. If the niblet 5 is excluded then a foil seal can be situated above the tablets 21, 22 or media 15. As shown in FIG. 5, this seal 23 can be the only seal so that a sample can be "scooped", pipetted or poured into the area between seal 12 and seal 23. To do so, seal 12 must be punctured before sampling or, alternatively, seal 12 can be excluded. If seal 12 and niblet 5 are excluded then after sampling seal 23 can be punctured to allow the sample to mix with the reagents.

Figure 6:
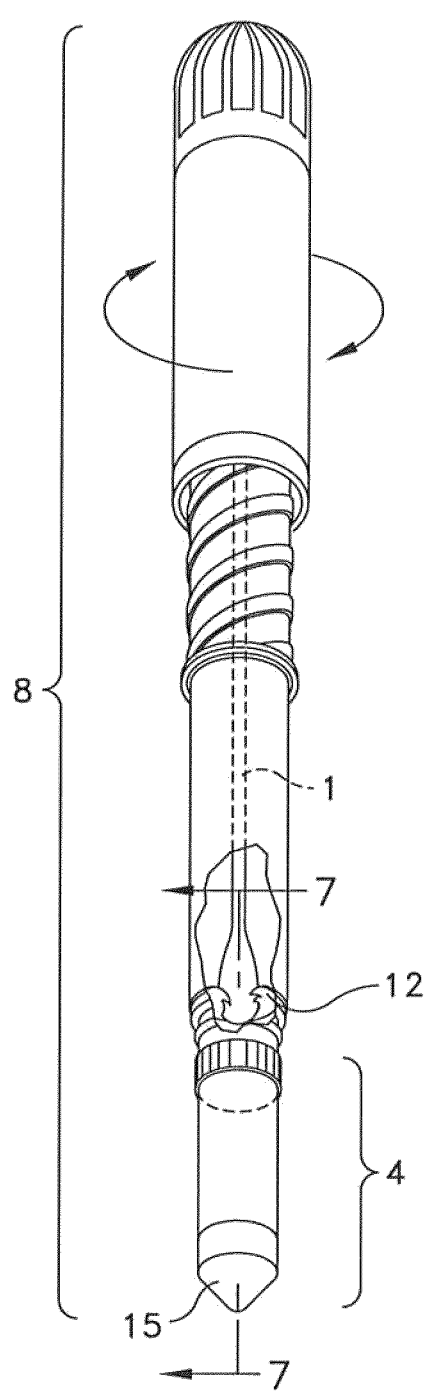
FIG. 6 shows the PocketSwab style device 8 with swab tip puncturing through the top seal 12 of the vial 4 and contacting the top seal 13 of the optional niblet 5 and the seal above a dried media/$E.$ $coli$ mixture 15 in the bottom of the vial 4.

FIG. 6 shows the PocketSwab style device 8 with swab tip puncturing through the top seal 12 of the vial 4 and contacting the top seal 13 of the optional niblet 5 and the seal above a dried media/*E. coli* mixture 15 in the bottom of the vial 4.

Figure 7:
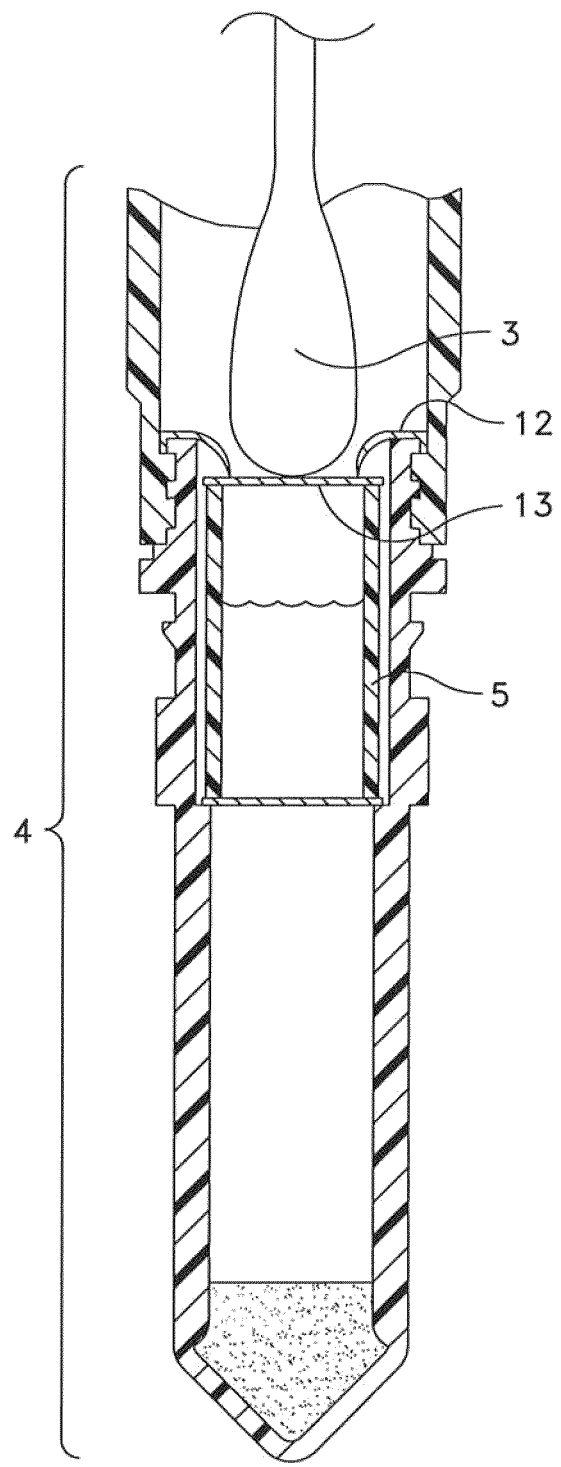
FIG. 7 is a cross-section with swab tip puncturing through the top seal 12 of the vial 4 and contacting the top seal 13 of the optional niblet 5 and the seal above a dried media/$E.$ $coli$ mixture 15 in the bottom of the vial 4.

FIG. 7 is a cross-section with swab tip puncturing through the top seal 12 of the vial 4 and contacting the top seal 13 of the optional niblet 5 and the seal above a dried media/*E. coli* mixture 15 in the bottom of the vial 4.

Figure 10:
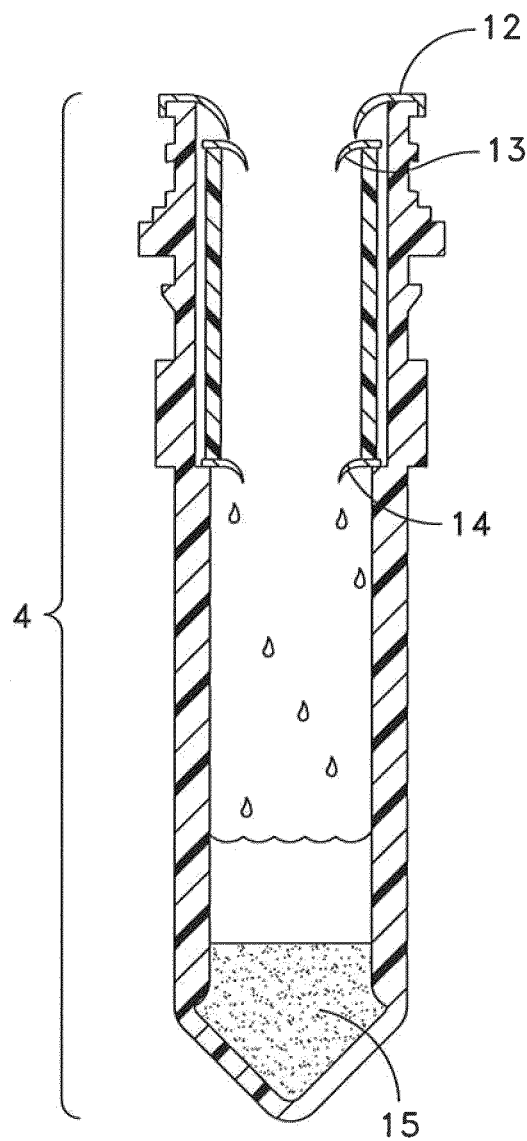
FIG. 10 is a cross-section showing the liquid from the niblet rehydrating the media/culture mixture 15 in the bottom of the vial 4.

FIGS. 8, 9 and 10 show the swab tip 3 puncturing through the various seals including the optional niblet seals to allow the liquid from the niblet to rehydrate the media/culture mixture 15 in the bottom of the vial 4.

Figure 11:
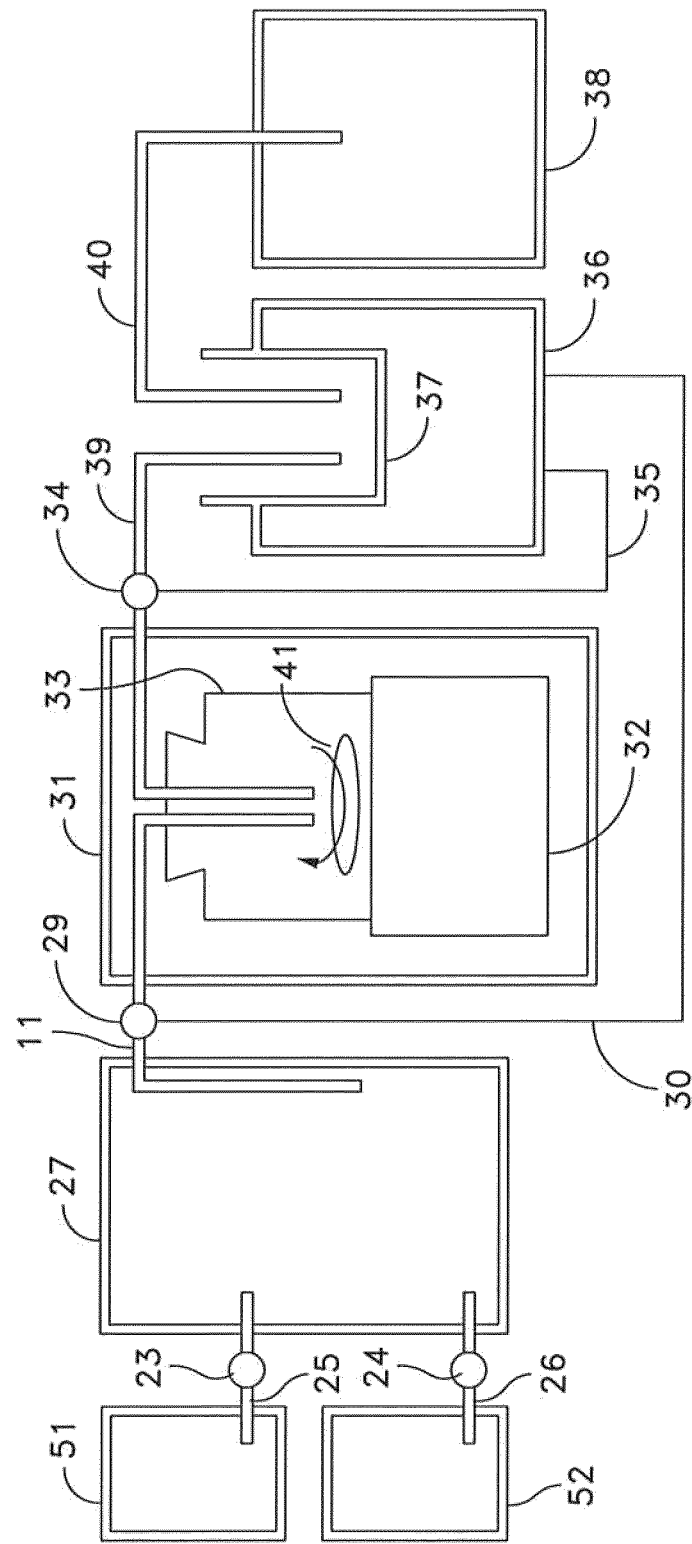
FIG. 11 is a flow diagram showing the flow of sample, media and culture, feedback loops and pumps.

FIG. 11 is a flow diagram showing the flow of sample, media and culture through an example of a continuous flow system. Media can flow from media container 51, through line 25 into reservoir 27. Sample can flow from sample container 52, through line 26 into reservoir 27. Pump 23 and pump 24 can be used to control the flow from sample container 52 and media container 51 into reservoir 27. Sample container 52 can be replaced by a valve, or other means, that diverts the flow of sample from its normal path into the system for testing. Within reservoir 27 media and sample can be mixed. The media/sample mixture can flow through line 28 into culture container 33. Flow control device 29 can control the flow of media/sample from reservoir 27 into culture container 33. Culture can flow, controlled by flow control device 34, out of culture container 33, through line 39 into testing container 37. Flow can also proceed from testing container 37 through line 40 to waste container 38. Flow control devices 34 and 29 can be controlled by feedback from measuring device 36. In a closed system pumps 34 and 29 are redundant and not both be needed and, in a closed system, could be placed in a variety of locations. Particularly in a closed system, the flow from reservoir 27 to culture container 33 and out from culture container 33 to waste container 38 can be maintained at the same rate. Culture can be maintained within culture container 33 by incubator 31. Mixing of culture, media and sample within culture container 33 can be facilitated by magnetic stirrer 32 and stir bar 41. Mixing can also occur within reservoir 27, media container 51 and sample container 52.

Figure 12:
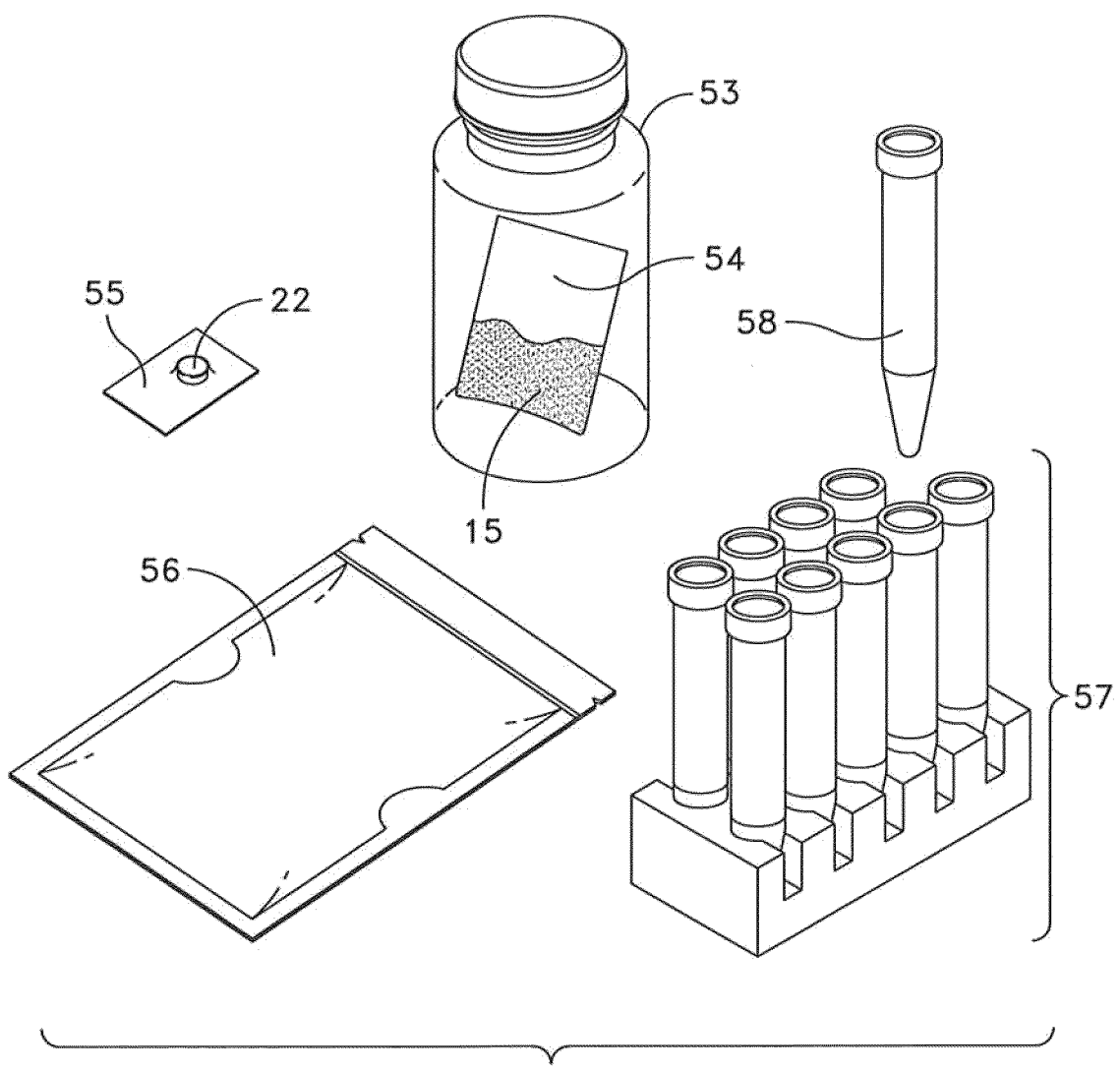
FIG. 12 shows three formats that can be used for testing, including a container, a plastic bag, and a series of tubes that can be used for a most probable number (MPN) type format using serial dilutions.

FIG. 12 shows a number of the different possible formats for conducting the individual sample tests for bacteriophage, including a container 53 with a dissolvable bag 54 of media 15 and a blister pack 55 containing a culture tablet 22 to be inserted; a compartmentalized bag 56; and a test tube 58 or most probable number system 57.

Figure 13:
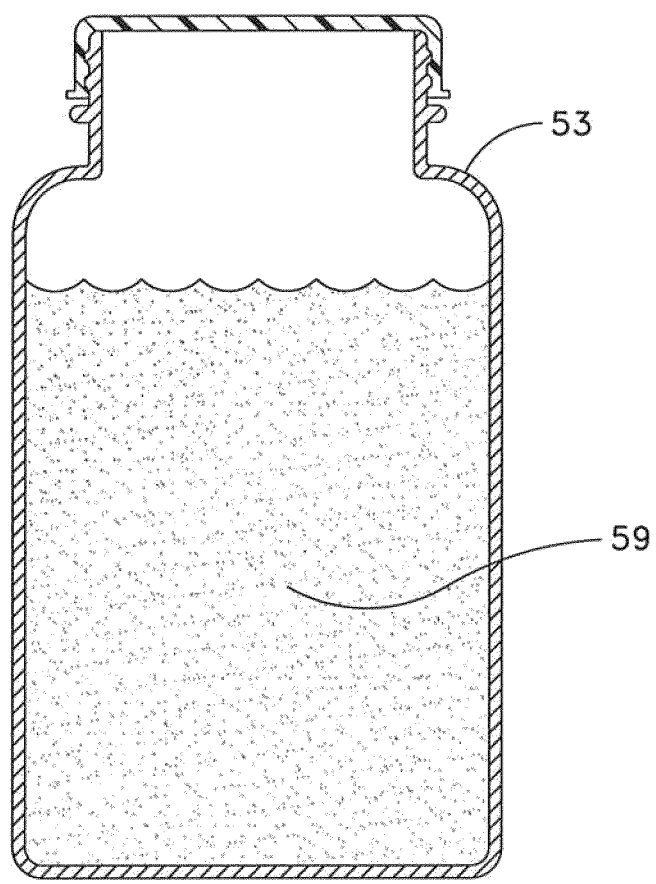
FIG. 13 shows the container format during testing with the sample, media, and bacterial culture mixture.

FIG. 13 shows the container 53 while being used during the testing procedure, containing a mixture 59 of the sample, culture and media.

EXAMPLES

Example 1

Media Formulation

The following formulation was found useful for an individual 100 ml water quality test (2.8 grams(g) media per test): 2 g LB broth; 0.01 g IPTG; 0.3 g Brain Heart Infusion; 0.5 tryptone; 0.007 g CaCl2; 0.003 g MgSO4; 0.025 g ONPG or 0.008 g Xgal For the PocketSwab format a tablet containing 23 milligrams (mg) of the above media was used.

*E. coli* Culture Formulation

Culturing was in a flask. *E. coli* strain C (ATCC 13706) was used and grown in the standard nutrient broth recommended by ATCC with 0.5% NaCl.

After culturing the *E. coli* culture was mixed 1:1 with 24% sucrose solution before freeze drying. After freeze drying the following material was combined with the freeze dried culture and the mixture tableted.

| Material | Percentage | Grams |
| --- | --- | --- |
| Dry Emdex (60-100) | 82.75 | 16.55 |
| Maltrin M-510 | 10.00 | 2.0 |
| PEG 8000 | 4.00 | 0.80 |
| Poly XL | 3.00 | 0.60 |
| Mg stearate | 0.25 | 0.05 |

Above formulation mixed for 5 minutes with bulk freeze dried *E. coli* culture and sifted using a sieve size of 60-E.

Example 2

The following results are from an experiment using various dilutions of somatic coliphage. Media used, per 100 mL, was 2 g LB broth; 0.01 g IPTG; 0.3 g Brain Heart Infusion; 0.007 g CaCl2; 0.003 g MgSO4; 0.025 g ONPG. In addition, a variety of concentrations of tryptone (tryp) (0.3 grams, 0.5 grams, and 0.75 grams) were used to assess the affect on test performance.

E. coli culture was E. coli strain C (ATCC 13706) grown in the standard nutrient broth recommended by ATCC with 0.5% NaCl.

PocketSwab format was used with neg: no color development, turbid=negative for coliphage
clear: no color development, no turbidity-positive for coliphage
(+/−): weak color development=positive for coliphage
(+): positive color development-positive for coliphage 0.5 mL of sample was pipetted into the bottom vial of the PocketSwab style device.

Results were as follows:

| SAMPLE | Phage/test | 0 tryp | 0.3 g tryp | 0.5 g tryp | 0.75 g tryp |
|---|---|---|---|---|---|
| neg control | 0 | neg | neg | neg | neg |
| $10^{-7}$ | 1 | neg | (+/−) | + | neg |
| $10^{-6}$ | 10 | + | + | + | + |
| $10^{-5}$ | 100 | + | + | + | + |
| $10^{-4}$ | 1,000 | + | + | + | + |
| $10^{-3}$ | 10,000 | + | + | + | + |
| $10^{-2}$ | 100,000 | + | + | + | + |
| $10^{-1}$ | 1,000,000 | (+/−) | (+/−) | (+/−) | (+/−) |
| Undiluted | 10,000,000 | clear | clear | clear | clear |

Example 3

The following results are from an experiment using various dilutions of somatic coliphage in a 100 mL sample. Tests were incubated for 3 hours at 37 degrees C. in a 160 mL screw top solid container with a vent to allow oxygen transfer.

Media used per 100 mL was 2 g LB broth; 0.01 g IPTG; 0.3 g Brain Heart Infusion; 0.007 g CaCl2; 0.003 g MgSO4; 0.008 g Xgal. In addition, a 0.5 grams tryptone was added to assess the affect on test performance. Tests were incubated for 3 hours at 37 degrees C. in a screw top solid container with a vent to allow gas exchange.

E. coli culture was E. coli strain C (ATCC 13706) grown in the standard nutrient broth recommended by ATCC with 0.5% NaCl.

neg: no color development, turbid=negative for coliphage
clear: no color development, no turbidity=positive for coliphage
(+/−): weak color development=positive for coliphage
(+): positive color development=positive for coliphage Results were as follows:

| SAMPLE | Phage/test | 0 tryp | 0.5 g tryp |
|---|---|---|---|
| neg control | 0 | neg | Neg |
| $10^{-8}$ | 0.1 | neg | Neg |
| $10^{-7}$ | 1 | (+/−) | + |
| $10^{-6}$ | 10 | + | + |
| $10^{-5}$ | 100 | + | + |
| $10^{-4}$ | 1,000 | + | + |
| $10^{-3}$ | 10,000 | + | + |
| $10^{-2}$ | 100,000 | + | + |
| $10^{-1}$ | 1,000,000 | (+/−) | (+/−) |
| Undiluted | 10,000,000 | clear | Clear |

Example 4

Continuous Flow System

Media Formulation 2 g LB broth; 0.01 g IPTG; 0.3 g Brain Heart Infusion; 0.5 tryptone; 0.007 g CaCl2; 0.003 g MgSO4; 0.025 g ONPG or 0.008 g Xgal; 0.01 g naladixic acid E. coli Culture Formulation Culturing was in a flask. E. coli strain C(CN-13) was used and grown in the standard nutrient broth recommended by ATCC with 0.5% NaCl.

After culturing the E. coli culture was mixed 1:1 with 24% sucrose solution before freeze drying. After freeze drying the following material was combined with the freeze dried culture and the mixture tableted.

| Material | Percentage | Grams |
|---|---|---|
| Dry Emdex (60-100) | 82.75 | 16.55 |
| Maltrin M-510 | 10.00 | 2.0 |
| PEG 8000 | 4.00 | 0.80 |
| Poly XL | 3.00 | 0.60 |
| Mg stearate | 0.25 | 0.05 |

Above formulation mixed for 5 minutes with bulk freeze dried E. coli culture and sifted using a sieve size of 60-E.

Example 5

Continuous Flow System

An alternative media formulation to that of Example 4 is as follows:

1.4 g media per test:
0.7 g LB broth; 0.01 g IPTG; 0.5 tryptone; 0.007 g CaCl2; 0.06 g MgSO4; 8 mg Xgal; 7 mg MUG-GAL; 0.01 g naladaxic acid; and 0.06 g sucrose.

Example 6

Continuous Flow System

The following tables include results from two different experiments using the culture from Example 4 and the media from Example 5.

Table 1 includes results from experiments with negative control sterile water. The initial time entry of −180 minutes represents the time for the culture to grow in log phase to the appropriate concentration for log phase growth: $0.5 \times 10^6$ to $0.5 \times 10^8$ per mL. As is shown in the table, the negative control flowed into the culture for 125 minutes. During that time the sample did not visually fluoresce. Although visual observation of fluorescence was used, it is expected that in an automated, continuous flow system, fluorescence will be measured by an instrument.

After a steady flow rate of 180 mL/hr was reached, the OD 520 nm was relatively stable and, therefore, no adjustment to the flow rate was made for the duration of the experiment.

TABLE 1

| Time (minutes) | Flow Rate mL/hr | Total Volume of Sample Tested | OD 520 nm | Visual Fluorescence |
|---|---|---|---|---|
| −180 | 0 | 0 | 0 | negative |
| 5 | 234 | 19.5 | 0.259 | negative |
| 20 | 246 | 80 | 0.237 | negative |
| 35 | 216 | 135 | 0.221 | negative |

TABLE 1-continued

| Time (minutes) | Flow Rate mL/hr | Total Volume of Sample Tested | OD 520 nm | Visual Fluorescence |
|---|---|---|---|---|
| 50 | 180 | 184 | 0.199 | negative |
| 65 | 180 | 225 | 0.222 | negative |
| 80 | 180 | 270 | 0.222 | negative |
| 95 | 180 | 315 | 0.219 | negative |
| 110 | 180 | 360 | 0.227 | negative |
| 125 | 180 | 405 | 0.236 | negative |

Table 2 includes results from experiments with a positive sample (~1-2 pfu/liter). The initial time entry of −180 minutes represents the time for the culture to grow to the appropriate concentration for log phase growth. As is shown in the table, visible fluorescence began to be observed at 315 minutes. From that point on fluorescence got stronger. Although visual observation of fluorescence was used, it is expected that in an automated, continuous flow system, fluorescence will be measured by an instrument. After a steady flow rate of 180 mL/hr was reached, the OD 520 nm increased steadily until the flow rate was increased to 240 mL/hr to offset the culture growth. After the flow rate was increased, the OD was reduced. In this experiment the flow rate was adjusted manually. It is expected that in an automated, continuous flow system, flow rate rate will be automatically adjusted based on target OD 520 readings. In addition, as can be seen by the last 2 readings at times 330 and 335, the OD dropped and flow rate stopped as the fluorescence strengthened. Thus, in addition to fluorescence, the flow rate and OD reductions could also be used as indicators of a positive result for coliphage.

TABLE 2

| Time | Flow Rate mL/hr | Total Volume of Sample Tested | OD 520 nm | Visual Fluorescence |
|---|---|---|---|---|
| −180 | 0 | 0 | 0 | negative |
| 5 | 234 | 19.5 | 0.298 | negative |
| 20 | 192 | 76 | 0.278 | negative |
| 35 | 192 | 123 | 0.263 | negative |
| 50 | 180 | 169 | 0.253 | negative |
| 65 | 180 | 210 | 0.260 | negative |
| 80 | 180 | 255 | 0.264 | negative |
| 95 | 180 | 300 | 0.247 | negative |
| 110 | 168 | 342 | 0.252 | negative |
| 125 | 168 | 384 | 0.250 | negative |
| 155 | 168 | 468 | 0.269 | negative |
| 185 | 168 | 552 | 0.272 | negative |
| 225 | 168 | 636 | 0.307 | negative |
| 255 | 168 | 720 | 0.354 | negative |
| 285 | 240 | 864 | 0.260 | negative |
| 315 | 204 | 966 | 0.207 | slight fluorescence |
| 320 | 204 | 977 | 0.193 | +fluorescence |
| 325 | 204 | 988 | 0.173 | +fluorescence |
| 330 | 66 | 993 | 0.119 | ++fluorescence |
| 335 | 0 | 993 | 0.110 | strong fluorescence |

Table 3 includes results for phage detection in waste water that was disinfected with chlorine to deliver a 4 log kill of coliform bacteria and then diluted with ground water to a final phage concentration of 1 pfu/200 ml. 6×100 ml sample replicates were tested. At 7 hours of incubation all samples had BTH (background too high). Thus, no detection could occur due to the test background overwhelming the system. In addition to being cultured for up to 7 hours, a 1 mL portion of each of the 6 samples were also transferred to 10 mL of fresh media and incubated through for a total of 9 hours total incubation (4 hours in first media and 5 hours in second media). At 7 hours (4 hours in first media and 3 hours in second media) only sample 6 was positive. After 8 hours (4 hours in first media and 4 hours in second media) samples 5 and 6 were positive. After 9 hours (4 hours in first media and 5 hours in second media) samples 2, 5 and 6 were positive. Spot plate testing confirmed samples 2, 5, and 6 contained phage. The results demonstrated that with sequential media additions test sensitivity could be increased.

TABLE 3

| Fluorescent Observation Time (hours) | Sample 1 | Sample 2 | Sample 3 | Sample 4 | Sample 5 | Sample 6 |
|---|---|---|---|---|---|---|
| 4 | − | − | − | − | − | − |
| 5 | − | − | − | − | − | − |
| 6 | − | − | − | − | − | − |
| 7 | BTH | BTH | BTH | BTH | BTH | BTH |
| Time from original sample addition | Sample Transfer Tube 1 | Sample Transfer Tube 2 | Sample Transfer Tube 3 | Sample Transfer Tube 4 | Sample Transfer Tube 5 | Sample Transfer Tube 6 |
| 7 | − | − | − | − | − | + |
| 8 | − | − | − | − | + | + |
| 9 | − | + | − | − | + | + |
| Spot Plate Confirmation of Phage in sample | − | + | − | − | + | + |

The invention claimed is:

1. A liquid assay method for detecting a bacteriophage in an unconcentrated or concentrated sample as an indicator of a hygienic quality of the sample, the method comprising:
   a. hydrating a media, the hydrated media providing:
      i. a nutrient for the growth of a fecal bacteria and the replication of the bacteriophage, the fecal bacteria characterized by its susceptibility to infection by the bacteriophage, and
      ii. an induction agent, the induction agent adapted for promoting intracellular enzyme production by the fecal bacteria;

b. mixing a culture of the fecal bacteria with a first volume of the hydrated media and the unconcentrated or concentrated sample to create a first admixture;

c. incubating the first admixture to create a first incubated admixture;

d. increasing detection of less prolific phage by adding at least a portion of the first incubated admixture with a volume of a second hydrated media to create a second admixture to reduce background signal resulting from growth of the fecal bacteria and natural lysis of the fecal bacteria not induced by the bacteriophage, wherein the second admixture comprises:
  i. a nutrient for the growth of the fecal bacteria,
  ii. an induction agent for promoting intracellular enzyme production by the fecal bacteria, and
  iii. an extracellular enzyme indicator, the extracellular enzyme indicator adapted for producing a detectable signal in the presence of an intracellular enzyme being released extracellularly from the lysis of fecal bacteria by the bacteriophage,
  wherein the second admixture allows for continued growth of the fecal bacteria and the addition of at least one indicator not present in the first incubated admixture;

e. incubating the second admixture; and f. detecting a signal from the indicator, when present, while the fecal bacteria continue to grow in the second admixture, the signal being present in the presence of the extracellular released enzyme, and wherein a detectable signal indicates the presence of the bacteriophage in the sample, the presence of the bacteriophage indicative of low hygienic quality of the sample.

2. The method of claim 1 further comprising stabilizing the fecal bacteria cell wall.

3. The method of claim 1 wherein the fecal bacteria is in the form of a concentrate selected from the group consisting of a tablet, powder, or gel.

4. The method of claim 1 wherein at least one of the hydrated media and second hydrated media is in the form of a concentrate selected from the group consisting of a tablet, powder, or gel.

5. The method of claim 1 wherein the bacteriophage comprises a coliphage, and wherein the bacterial culture comprises *Escherichia coli*.

6. The method of claim 1 wherein the intracellular enzyme comprises β-galactosidase.

7. The method of claim 1 wherein the induction agent increases bacteriophage infection rates of the fecal bacteria.

8. The method of claim 1 wherein the induction agent comprises isopropyl-β-D-thiogalactoside.

9. The method of claim 1 wherein the sample comprises a liquid and wherein the liquid has sufficient volume to hydrate both the media and the bacteria.

10. The method of claim 1 wherein the sample is a non-liquid sample or a sample with insufficient sample volume, and the method further comprising hydrating said non-liquid sample or said sample with insufficient sample volume.

11. The method of claim 1 wherein the extracellular enzyme indicator comprises both a color indicator and a fluorescent indicator.

12. The method of claim 11 wherein the color indicator comprises a 5-bromo-4-chloro-3-indoyl-β-D-glactoside and wherein the fluorescent indicator comprises a 4-methylumbelliferyl-β-D-galactopyranoside.

13. The method of claim 1 wherein hydrating the media comprises solubilizing a water soluble container of a dry media.

14. The method of claim 1 wherein mixing the culture of said fecal bacteria with the hydrated media comprises solubilizing a water soluble container of a dry culture of said fecal bacteria.

15. The method of claim 1 wherein hydrating a media comprises solubilizing a water soluble container of both a dry media and a dry bacterial culture.

16. The method of claim 1 wherein the time to obtain the signal is less than about 8 hours.

17. The method of claim 1 wherein the time to obtain the signal is between about 3 to about 6 hours.

18. The method of claim 1 wherein diluting at least a portion of the first incubated admixture for enhancing bacteriophage detection results in reducing background fluorescence.

19. The method of claim 1 wherein diluting at least a portion of the first incubated admixture for enhancing bacteriophage detection results in increasing testing time.

* * * * *